United States Patent
Sano et al.

(10) Patent No.: US 9,695,413 B2
(45) Date of Patent: Jul. 4, 2017

(54) RNA PREPARATION METHOD

(71) Applicants: KANEKA CORPORATION, Osaka (JP); BIOCOSM INC., Osaka (JP)

(72) Inventors: Sotaro Sano, Takasago (JP); Shigehiko Miyamoto, Takasago (JP); Jun Tomono, Takasago (JP); Hajime Hiratsuka, Osaka (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 14/437,936

(22) PCT Filed: Oct. 25, 2013

(86) PCT No.: PCT/JP2013/078939
§ 371 (c)(1),
(2) Date: Apr. 23, 2015

(87) PCT Pub. No.: WO2014/065395
PCT Pub. Date: May 1, 2014

(65) Prior Publication Data
US 2015/0376600 A1    Dec. 31, 2015

(30) Foreign Application Priority Data
Oct. 26, 2012  (JP) ................. 2012-237057

(51) Int. Cl.
| C07H 21/00 | (2006.01) |
| C12N 15/10 | (2006.01) |
| C12Q 1/68 | (2006.01) |
| C07H 1/06 | (2006.01) |
| C07H 1/08 | (2006.01) |

(52) U.S. Cl.
CPC ....... C12N 15/1003 (2013.01); C12Q 1/6806 (2013.01); *C07H 1/06* (2013.01); *C07H 1/08* (2013.01)

(58) Field of Classification Search
None
See application file for complete search history.

(56) References Cited

U.S. PATENT DOCUMENTS

| 2004/0019196 A1 | 1/2004 | Bair, Jr. et al. |
| 2006/0105372 A1 | 5/2006 | Bair et al. |
| 2008/0003575 A1 | 1/2008 | Michalik et al. |
| 2010/0035331 A1* | 2/2010 | Tsuchiya ............ C12N 15/1006 435/270 |

FOREIGN PATENT DOCUMENTS

| JP | 2004000922 A | 1/2004 |
| JP | 4836795 B2 | 12/2011 |
| WO | WO-2007/049326 A1 | 5/2007 |
| WO | WO-2007/116450 A1 | 10/2007 |
| WO | WO-2010/083844 A1 | 7/2010 |
| WO | WO-2012/108471 A1 | 8/2012 |

OTHER PUBLICATIONS

Partanen Acta Chemical Scandinavia (1998), vol. 52, p. 985-994.*
"Derivative." Merriam-Webster.com. Merriam-Webster, n.d. Web. Mar. 25, 2016.*
"Organic." Merriam-Webster.com. Merriam-Webster, n.d. Web. Aug. 25, 2016.*
Singh et al. J. Plant Biochemistry & biotechnology (2009), vol. 18, pp. 77-81.*
Tzanetakis et al. Journal of Virological Methods (2008), vol. 149, pp. 167-170.*
Hirano et al. Biopolymers (2011) vol. 97, pp. 117-122.*
Shirzadegan et al., "An efficient method for isolation of RNA from tissue cultured plant cells", Nucleic Acids Research, 1991,vol. 19, No. 21, p. 6055.
Chomczynski et al., "Singe-step Method of RNA Isolation by Acid Guanidinium Thiocyanate-Phenol-Chloroform Extraction" Analytical Biochemistry, 162, 156-159 (1987).
Bio Experiment Illustrated, (7), 2003.
English translation of International Preliminary Report on Patentability issued Apr. 28, 2015 in PCT/JP2013/078939.

* cited by examiner

*Primary Examiner* — Patrick Lewis
(74) *Attorney, Agent, or Firm* — Polsinelli PC

(57) ABSTRACT

An object of the present invention is to provide a technique for preparing RNA ready for an enzymatic reaction more easily than conventional techniques. The present invention provides a reagent for RNA extraction from a biological sample which contains an alkali metal salt and a surfactant.

3 Claims, 1 Drawing Sheet

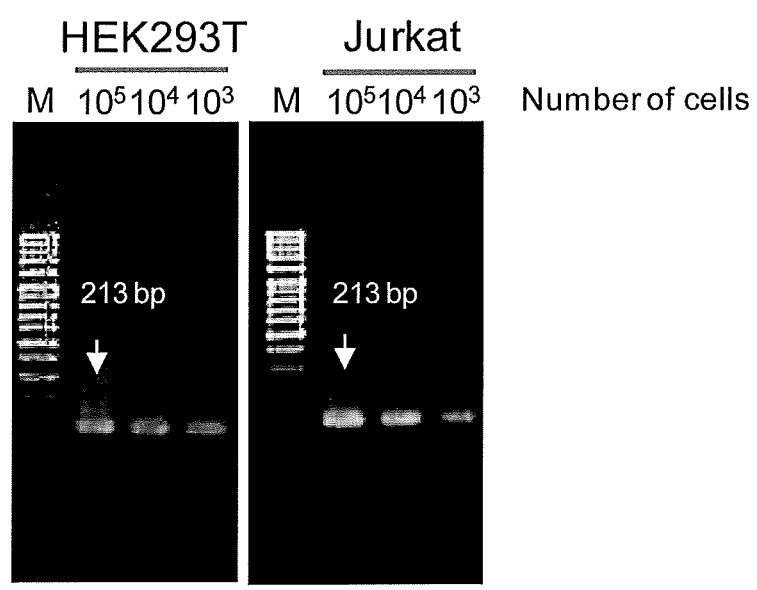

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthesized

```
<400> SEQUENCE: 1
ggcctcactt gcctcctgca a                                      21

<210> SEQ ID NO 2
<211> LENGTH: 21
<212> TYPE: DNA
<213> ORGANISM: Artificial Sequence
<220> FEATURE:
<223> OTHER INFORMATION: Synthesized

<400> SEQUENCE: 2
gcaagagtgc gccctctact g                                      21

<210> SEQ ID NO 3
<211> LENGTH: 17
<212> TYPE: DNA
<213> ORGANISM: Artificial Sequence
<220> FEATURE:
<223> OTHER INFORMATION: Synthesized

<400> SEQUENCE: 3
agatggccac ggctgct                                           17

<210> SEQ ID NO 4
<211> LENGTH: 19
<212> TYPE: DNA
<213> ORGANISM: Artificial Sequence
<220> FEATURE:
<223> OTHER INFORMATION: Synthesized

<400> SEQUENCE: 4
aaccgctcat tgccaatgg                                         19
```

RNA PREPARATION METHOD

CROSS REFERENCE TO RELATED APPLICATIONS

This application is a National Phase filing under 35 U.S.C. §371 of PCT/JP2013/078939 filed on Oct. 25, 2013; and this application claims priority to Application No. 2012-237057 filed in Japan on Oct. 26, 2012. The entire contents of each application are hereby incorporated by reference.

TECHNICAL FIELD

The present invention relates to a method for extracting undegraded RNA from a biological sample, which makes use of a reagent for RNA extraction containing an alkali metal salt and a surfactant.

BACKGROUND ART

Developments in genetic engineering have made it possible to use genetic testing in applications such as virus detection, analysis of cell kinetics, predisposition testing, and drug response testing. RNA, which is one of the targets for genetic testing in these applications, is more unstable than DNA and can be easily degraded by endogenous ribonucleases contained in biological samples or when subjected to high-temperature/alkali treatment. Thus, high technologies, multi-step procedures, and expensive dedicated devices and reagents for preventing degradation of RNA have been required to prepare RNA.

For example, the following may be mentioned as known typical methods for recovering RNA from a biological sample: the acid guanidium-phenol-chloroform (AGPC) method (Non Patent Literature 1) which makes use of a combination of a protein denaturing agent and an organic solvent to dissolve the analyte and inactivate endogenous ribonucleases, thereby recovering the undegraded RNA; and the hot phenol method (Non Patent Literature 2). Unfortunately, both the methods are not only risky because of the use of an organic solvent and a high concentration of denaturing agent for inhibiting enzymatic reactions such as nucleic acid amplification, but also require a long-term, multi-step procedures to remove these materials, which is disadvantageous in terms of cost and ease of implementation.

Some techniques for easily preparing RNA have also been developed in which a strong chaotropic substance and a surfactant as protein denaturing agents are used to extract RNA, without using organic solvents, which extract is then directly subjected to an enzymatic reaction. For example, a method is known in which a biological sample is dissolved using guanidine thiocyanate and sarkosyl as denaturing agents, and then RNA is extracted while protecting RNA from degradation by endogenous ribonucleases (Patent Literature 1). The resulting extract can be directly subjected to an enzymatic reaction. These techniques facilitate the extraction of RNA compared to conventional techniques, by eliminating the need of steps for removing the denaturing agents before the extract is subjected to an enzymatic reaction. However, since the strong chaotropic substance, such as guanidine thiocyanate, and sarkosyl are strong protein denaturing agents, the presence of such strong denaturing agents in an enzymatic reaction system is undesirable in terms of efficiency of enzymatic reactions.

As a countermeasure to this, a nucleic acid extraction method that uses cholic acid or glycolic acid in order not to inhibit a subsequent enzymatic reaction has been known (Patent Literature 2). This technique eliminates the need of steps for purifying or diluting the nucleic acid extracted from a biological sample, and the nucleic acid can be directly subjected to an enzymatic reaction such as nucleic acid amplification. Unfortunately, this technique cannot prevent RNA degradation by endogenous ribonucleases and thus does not allow undegraded RNA to be extracted.

CITATION LIST

Patent Literature

Patent Literature 1: Japanese Patent No. 4836795
Patent Literature 2: WO 2007/116450

Non Patent Literature

Non Patent Literature 1: Chomczynski and Sacchi, 1987, Analytical Biochemistry, 162: 156-159.
Non Patent Literature 2: Takayuki Mizuno, 2003, Bio Experiment Illustrated (7)

SUMMARY OF INVENTION

Technical Problem

An object of the present invention is to provide a technique for preparing RNA ready for an enzymatic reaction more easily than conventional techniques.

Solution to Problem

The present invention relates to a reagent for RNA extraction from a biological sample, containing an alkali metal salt and a surfactant.

The alkali metal salt is preferably an alkali metal halide.
The alkali metal salt is preferably lithium chloride.
Preferably, the surfactant includes glycolic acid or its derivatives.
Preferably, the surfactant further includes deoxycholic acid or its derivatives.
The present invention also relates to a kit for RNA extraction, including the reagent.
The present invention further relates to a method for RNA extraction from a biological sample, including using the reagent or the kit for RNA extraction.

Advantageous Effects of Invention

According to the present invention, undegraded RNA that is ready for an enzymatic or chemical reaction or the like can be more easily prepared than conventional methods.

BRIEF DESCRIPTION OF DRAWINGS

The FIGURE shows the results of RT-PCR of the RNAs extracted from cell samples.

DESCRIPTION OF EMBODIMENTS

The following description is offered to illustrate the present invention in detail.

According to the present invention, an alkali metal salt and a surfactant are used to prepare undegraded RNA from a biological sample. This allows RNA ready for a subsequent enzymatic reaction to be prepared while preventing degradation of RNA by endogenous ribonucleases in the sample.

The biological sample used in the present invention may be anything that contains a nucleic acid and examples include, but are not limited to, animal and plant cells and tissues, biological fluids, e.g., whole blood, serum, lymph, tissue fluid, urine, semen, vaginal secretions, amniotic fluid, tears, saliva, and sweat, cell-derived vesicles such as exosomes, stool, sputum, bacteria, and viruses.

The RNA used in the present invention may be any RNA that contains a ribonucleotide polymer and examples include, but are not limited to, messenger RNA and non-translatable RNA such as transfer RNA, ribosomal RNA, small nuclear RNA, small nucleolar RNA, and micro RNA.

Commonly, RNA is prepared by a method that is based on adsorption of RNA on a solid phase carrier, or a method that is based on addition of an organic solvent, water-soluble polymer, or surfactant to insolubilize RNA. Unfortunately, these methods not only require a complicated process for purifying the treated solution, but also show variations in recovery efficiency depending on the molecular weight of RNA, in which a target RNA may not be obtained in some cases. In contrast, an advantage of the RNA preparation method of the present invention is that the RNA extract can be directly subjected to a subsequent analysis, and this treated solution contains all the RNA molecules originally contained in the sample, without losses.

According to the present invention, the reagent for RNA extraction contains an alkali metal salt as an RNA protecting agent.

Examples of the alkali metal salt used in the present invention include lithium salts, sodium salts, potassium salts, rubidium salts, and cesium salts. Preferred examples include, but are not limited to, lithium chloride, lithium bromide, lithium iodide, lithium acetate, lithium hydroxide, sodium fluoride, sodium chloride, sodium bromide, sodium iodide, sodium acetate, sodium pyrophosphate, sodium thiocyanate, sodium sulfate, sodium sulfite, sodium disulfite, sodium dihydrogen phosphate, sodium hydrogen carbonate, sodium tartrate, sodium nitrate, potassium fluoride, potassium chloride, potassium bromide, potassium iodide, potassium acetate, potassium hydrogen phosphate, potassium sulfate, rubidium fluoride, rubidium chloride, rubidium bromide, rubidium iodide, rubidium acetate, cesium chloride, cesium bromide, cesium iodide, and cesium acetate. More preferred examples include alkali metal halides. Lithium chloride, which has less chaotropic effect, is still more preferred among halides. These alkali metal salts may be used alone or in combination.

Besides its RNA protecting effect, the alkali metal salt has the advantage that it is less likely to affect enzymatic activity than other metal salts that generate polyvalent cations which can be cofactors of nucleic acid-related enzymes because the alkali metal salt does not form such a cofactor.

One skilled in the art will be able to easily determine an optimum alkali metal salt concentration in the reagent for RNA extraction. For example, the concentration is preferably at least 0.2 M but not higher than the saturated concentration, more preferably at least 0.3 M but not higher than 5.0 M, and still more preferably at least 0.3 M but not higher than 2.5 M. If the alkali metal salt concentration is too low, RNA cannot be protected from degradation by endogenous ribonucleases; if the concentration is too high, RNA can be protected but the alkali metal salt tends to inhibit a subsequent enzymatic reaction.

According to the present invention, the reagent for RNA extraction contains a surfactant as an analyte solubilizer. Examples of the surfactant used in the present invention include ionic surfactants, non-ionic surfactants, and amphoteric surfactants. Preferred examples include Tween series surfactants such as Tween 20, Tween 40, Tween 60, and Tween 80, Triton series surfactants such as Triton X-100, Triton X-114, and Triton XL-80N, Nonidet series surfactants, non-ionic surfactants such as NP-40, and anionic surfactants such as cholic acid or its derivatives, deoxycholic acid or its derivatives, and glycolic acid or its derivatives. More preferred are Tween 20, Triton X-100, deoxycholic acid, and glycolic acid. The surfactant is not limited to these examples, and any surfactant can be used as long as it does not inhibit enzymatic reactions. These surfactants may be used alone or in combination.

One skilled in the art will be able to easily determine an optimum surfactant concentration in the reagent for RNA extraction. In the case of using cholic acid or its derivatives, deoxycholic acid or its derivatives, or glycolic acid or its derivatives, the concentration is preferably not lower than 1 mM. If the surfactant concentration is too low, the biological sample tends not to be dissolvable in the reagent.

According to the present invention, the reagent for RNA extraction may contain a buffer. Suitable examples of buffers that can be used in the present invention include phosphate buffers and Good's buffers. Preferred among these are Good's buffers such as MES, Bis-Tris, ADA, PIPES, ACES, MOPSO, BES, MOPS, TES, HEPES, DIPSO, TAPSO, POPSO, HEPPSO, EPPS, Tricine, Tris, Bicine, TAPS, CHES, CAPSO, and CAPS, with TAPS being particularly preferred. These buffers may be used alone or in combination.

According to the present invention, the reagent for RNA extraction may contain a protein component such as albumin, or polyamine, cyclodextrin, trehalose, a water-soluble polymer such as polyvinylpyrrolidone (PVP) or polyethylene glycol, which have an effect in reducing inhibition of enzymatic reactions by unnecessary components originating from a biological sample.

According to the present invention, the reagent for RNA extraction may contain an antifreeze, such as glycerol, betaine, or sucrose, to prevent freezing at sub-zero temperatures.

According to the present invention, the reagent for RNA extraction may contain an agent a chelating agent, a nuclease inhibitor, or a reducing agent (e.g. DTT (dithiothreitol)) for further ensuring inactivation of nucleases, and an organic solvent (e.g. DMSO or formamide) for a subsequent enzymatic reaction.

The biological sample and the reagent for RNA extraction are preferably mixed at a ratio of 9:1 to 1:999, more preferably 4:1 to 1:499, and still more preferably 1:1 to 1:99.

In the present invention, after mixing the biological sample and the reagent for RNA extraction, the biological sample may be physically disrupted in the RNA extraction. For example, the RNA extraction may be combined with freeze-thaw disruption, physical disruption with a homogenizer, or the like. Moreover, according to the present invention, RNA can be extracted without the need of disruption prior to mixing the biological sample and the reagent for RNA extraction.

After mixing the biological sample and the reagent for RNA extraction, heat treatment may be carried out to extract RNA from the biological sample. The heat treatment temperature is preferably at least 0° C. but not higher than 100° C., more preferably at least 30° C. but not higher than 90°

C., and still more preferably at least 50° C. but not higher than 80° C. At too low temperatures, extraction efficiency tends to be reduced; at too high temperatures, RNA tends to degrade. The period of the heat treatment is preferably not longer than 30 minutes, more preferably not longer than 15 minutes. If the treatment period is too short, extraction efficiency tends to be reduced; if the treatment period is too long, RNA tends to degrade.

According to the present invention, the RNA extract can be directly mixed as a substrate with an enzymatic reaction solution to initiate an enzymatic reaction such as nucleic acid amplification, without further performing purification, dilution or other steps. Examples of enzymes that can be used for the reaction include nucleases such as deoxyribonucleases, ribonucleases, exonucleases, and endonucleases; proteases such as proteinases and peptidases; polymerases such as DNA-dependent DNA polymerases, RNA-dependent DNA polymerases, DNA-dependent RNA polymerases, RNA-dependent RNA polymerases, heat resistant polymerases, strand-displacement polymerases, and terminal transferases; and ligases, recombinases, lysozymes, and cellulases. The RNA extract and the enzymatic reaction solution are preferably mixed at a ratio of 1:999 to 999:1, more preferably 1:99 to 99:1, and still more preferably 1:49 to 49:1.

According to the present invention, the RNA extract may be mixed with a fluorescent nucleic acid labelling reagent or a fluorescent labelling probe (e.g. ethidium bromide, SYBR® Green, PicoGreen®) to detect the RNA contained therein. Or, the RNA extract may be subjected to a nucleic acid amplification reaction in the presence of a fluorescent labelling reagent to monitor the amplification reaction in real time. Alternatively, the RNA extract may be subjected to a sequencing reaction.

The term "nucleic acid amplification reaction" used herein refers to a technique for amplifying a nucleic acid sequence, as typified by PCR. Known examples other than PCR include, but are not limited to, ligase chain reaction (LCR), strand displacement amplification (SDA), rolling circle amplification (RCA), cycling probe technology (CPT), Q-beta replicase amplification technology, isothermal and chimeric primer-initiated amplification of nucleic acids (ICAN), loop-mediated isothermal amplification of DNA (LAMP), nucleic acid sequence-based amplification method (NASBA), and transcription mediated amplification method (TMA).

According to the present invention, the target nucleic acid in the RNA extract may be mixed with a molecule having a specific binding ability, e.g., a molecule containing a nucleic acid sequence complementary to apart of the target nucleic acid, an antibody, or a single-stranded nucleic acid-binding protein, to specifically bind to each other; in other words, the RNA extract may be used in, for example, Southern blotting, Northern blotting, real-time PCR, or specific labelling, detection, purification or isolation using a labeled nucleic acid probe or the like.

According to the present invention, the RNA extract may be subjected to various chromatography techniques such as ion exchange column chromatography or gel permeation column chromatography, centrifugation, filtration, dialysis, or adsorption on a solid phase carrier to remove unnecessary components and thereby purify the RNA in the RNA extract. These techniques may also be appropriately combined for use as a RNA purification kit.

The kit of the present invention contains the reagent for RNA extraction. In addition, the kit may contain, for example, a sample washing solution, a deoxyribonuclease, a protease, a reverse transcriptase, a DNA polymerase and its substrate, and an oligonucleotide.

The reagent and kit of the present invention can also be incorporated into a nucleic acid preparation device, a nucleic acid amplification device, a nucleic acid autoanalyzer, or the like.

EXAMPLES

The following examples are given to more specifically illustrate the present invention. It should be noted that the present invention is not limited only to these examples.

Example 1

Following the procedure described below, RNA was extracted from mouse blood, and RT-PCR was performed using the extracted RNA as a template. Agarose gel electrophoresis was then performed to confirm the presence of an amplified fragment derived from the RNA.

(Preparation of Reagent for RNA Extraction)

Reagents for RNA extraction having the following compositions were prepared:
lithium chloride, 75 mM TAPS (pH 8.0), 2.25 mM $CaCl_2$, 15 mM $MgCl_2$, 175 mM glycolic acid, 5 mM deoxycholic acid, 50 mM EDTA, and 0.05% Triton X-100.

The reagents for RNA extraction were prepared to have different lithium chloride concentrations of 0 M, 0.1 M, 0.2 M, 0.5 M, 1.0 M, 2.0 M, 3.0 M, 4.0 M, 5.0 M, 6.0 M, and 7.0 M.

(Extraction of RNA)

Blood was collected from a mouse. The anticoagulant used was heparin. The reagents for RNA extraction (18 µl each) were individually added to 2 µl portions of the mouse blood, and incubated at 75° C. for 5 minutes. After incubation, the solutions were cooled to room temperature, mixed with 2 µl (corresponding to 10 Units) of DNase I, and incubated at 42° C. for 5 minutes and then at 75° C. for 10 minutes.

(RT-PCR)

The RNA samples prepared above were cooled to room temperature, and RT-PCR was performed using the samples as templates to obtain an amplified nucleic acid fragment derived from the analyte. The target of RT-PCR was H3F3A mRNA, and the primer set used was Forward Primer F1 (5'-GGCCTCACTTGCCTCCTGCAA-3'; SEQ ID NO:1) and Reverse Primer R1 (5'-GCAAGAGTGCGCCCTC-TACTG-3'; SEQ ID NO:2). The RT-PCR was carried out using PrimeScript One Step RT-PCR Kit Ver. 2 (Takara Bio, Inc.), and the RNA samples prepared above were individually added in an amount of 2% by volume to a reaction solution and subjected to the RT-PCR. The reaction consisted of reverse transcription at 50° C. for 30 minutes, and inactivation of the reverse transcriptase at 94° C. for 1 minute, followed by 30 PCR cycles of: 94° C. for 15 seconds; 62° C. for 15 seconds; and then 72° C. for 15 seconds. As a negative control, 30 PCR cycles of: 94° C. for 15 seconds; 60° C. for 15 seconds; and then 72° C. for 15 seconds were also performed without performing reverse transcription, to confirm that the amplified fragment was not derived from DNA. Next, the RT-PCR products were subjected to common agarose gel electrophoresis to visualize the amplified fragment.

Table 1 shows the results of visualization of the amplified fragment by agarose gel electrophoresis. The results demonstrate that in the case of the reagents for RNA extraction with a lithium chloride concentration of 0.5 to 5.0 M, only the RT-PCR produced an amplified fragment. This indicates that the RNA was properly extracted.

TABLE 1

| Concentration of LiCl (M) | 0 | 0.1 | 0.2 | 0.5 | 1.0 | 2.0 | 3.0 | 4.0 | 5.0 | 6.0 | 7.0 |
|---|---|---|---|---|---|---|---|---|---|---|---|
| RT-PCR | − | − | − | + | + | + | + | + | + | − | − |

+: amplified
−: not amplified

Example 2

Following the procedure described below, RNA was extracted from mouse blood, and RT-PCR was performed using the extracted RNA as a template. Agarose gel electrophoresis was then performed to confirm the presence of an amplified fragment derived from the RNA.
(Preparation of Reagent for RNA Extraction)

Reagents for RNA extraction having the following compositions with different alkali metal salts were prepared: 0.7 M alkali metal salt, 75 mM TAPS (pH 8.0), 2.25 mM $CaCl_2$, 15 mM $MgCl_2$, 175 mM glycolic acid, 5 mM deoxycholic acid, 50 mM EDTA, and 0.05% Triton X-100.

The alkali metal salts used were lithium chloride, lithium bromide, lithium iodide, sodium chloride, sodium iodide, potassium chloride, potassium iodide, rubidium chloride, cesium chloride, lithium acetate, sodium dihydrogen phosphate, sodium tartrate, sodium nitrate, potassium acetate, potassium hydrogen phosphate, and potassium sulfate.

Another reagent for RNA extraction containing lithium chloride as an alkali metal salt and free from the surfactant deoxycholic acid was prepared.
(Extraction of RNA)

Using the prepared reagents for RNA extraction and following the same procedure as in Example 1, RNA was extracted from blood collected from a mouse.
(RT-PCR)

Following the same procedure as in Example 1, RT-PCR was performed using the RNA samples extracted above as templates to obtain an amplified nucleic acid fragment derived from the analyte.

Table 2 shows the presence or absence of amplification visualized by agarose gel electrophoresis. The results demonstrate that in the case of the reagents for RNA extraction containing an alkali metal salt, only the RT-PCR produced an amplified fragment. This indicates that the RNA was properly extracted. Moreover, in the case of the reagents for RNA extraction containing an alkali metal halide, among other alkali metal salts, the amplification efficiency of RT-PCR was high. The results further demonstrate that these reagents for RNA extraction did not inhibit the DNase I treatment, RT reaction, and PCR.

TABLE 2

| | RNA protecting agent | Surfactant | RT-PCR | PCR |
|---|---|---|---|---|
| Example 2 | Lithium chloride | Deoxycholic acid, glycolic acid, Triton X-100 | + | − |
| | Lithium bromide | Deoxycholic acid, glycolic acid, Triton X-100 | + | − |
| | Lithium iodide | Deoxycholic acid, glycolic acid, Triton X-100 | + | − |
| | Sodium chloride | Deoxycholic acid, glycolic acid, Triton X-100 | + | − |
| | Sodium iodide | Deoxycholic acid, glycolic acid, Triton X-100 | + | − |
| | Potassium chloride | Deoxycholic acid, glycolic acid, Triton X-100 | + | − |
| | Potassium iodide | Deoxycholic acid, glycolic acid, Triton X-100 | + | − |
| | Rubidium chloride | Deoxycholic acid, glycolic acid, Triton X-100 | + | − |
| | Cesium chloride | Deoxycholic acid, glycolic acid, Triton X-100 | + | − |
| | Lithium acetate | Deoxycholic acid, glycolic acid, Triton X-100 | + | − |
| | Sodium dihydrogen phosphate | Deoxycholic acid, glycolic acid, Triton X-100 | + | − |
| | Sodium tartrate | Deoxycholic acid, glycolic acid, Triton X-100 | + | − |
| | Sodium nitrate | Deoxycholic acid, glycolic acid, Triton X-100 | + | − |
| | Potassium acetate | Deoxycholic acid, glycolic acid, Triton X-100 | + | − |
| | Potassium hydrogen phosphate | Deoxycholic acid, glycolic acid, Triton X-100 | + | − |
| | Potassium sulfate | Deoxycholic acid, glycolic acid, Triton X-100 | + | − |
| | Lithium chloride | Glycolic acid, Triton X-100 | + | − |
| Comparative Example 1 | Magnesium chloride | Deoxycholic acid, glycolic acid, Triton X-100 | − | − |
| | Potassium chloride | Deoxycholic acid, glycolic acid, Triton X-100 | − | − |
| | Nickel chloride | Deoxycholic acid, glycolic acid, Triton X-100 | − | − |
| | Manganese chloride | Deoxycholic acid, glycolic acid, Triton X-100 | − | − |
| | Urea | Deoxycholic acid, glycolic acid, Triton X-100 | + | + |
| | Guanidine hydrochloride | Deoxycholic acid, glycolic acid, Triton X-100 | + | + |
| | Guanidine thiocyanate | Deoxycholic acid, glycolic acid, Triton X-100 | + | + |
| | Diammonium hydrogen phosphate | Deoxycholic acid, glycolic acid, Triton X-100 | + | + |
| | Not used | Deoxycholic acid, glycolic acid, Triton X-100 | − | − |
| Comparative Example 2 | Lithium chloride | Not used | + | + |

+: amplified
−: not amplified

Comparative Example 1

Following the procedure described below, RNA was extracted from mouse blood, and RT-PCR was performed using the extracted RNA as a template. Agarose gel electrophoresis was then performed to confirm the presence of an amplified fragment.
(Preparation of Reagent for RNA Extraction)

Reagents for RNA extraction having the following compositions with different strong chaotropic substances or polyvalent metal salts or an ammonium salt were prepared: 0.7 M strong chaotropic substance, polyvalent metal salt or ammonium salt, 75 mM TAPS (pH 8.0), 2.25 mM $CaCl_2$, 15 mM $MgCl_2$, 175 mM glycolic acid, 5 mM deoxycholic acid, 50 mM EDTA, and 0.05% Triton X-100.

The strong chaotropic substances used were guanidine thiocyanate, guanidine hydrochloride, and urea. The polyvalent metal salts used were magnesium chloride, calcium chloride, nickel chloride, and manganese chloride. The ammonium salt used was diammonium hydrogen phosphate. Another reagent for RNA extraction containing the surfactants alone, without the RNA protecting agent salts, was prepared.
(Extraction of RNA)
Using the prepared reagents for RNA extraction and following the same procedure as in Example 1, RNA was extracted from blood collected from a mouse.
(RT-PCR)
Following the same procedure as in Example 1, RT-PCR was performed using the RNA samples extracted above as templates.

Table 2 shows the results of visualization of the amplified fragment by agarose gel electrophoresis. The results demonstrate that in the case of using the polyvalent metal salts, neither the RT-PCR nor PCR produced an amplified fragment. This indicates that the polyvalent metal ions did not function as RNA protecting agents, or inhibited the enzymatic reactions. Accordingly, the polyvalent cations are not preferred as additives for the reagents for RNA extraction in the present system. The results also demonstrate that in the case of using the strong chaotropic substances or ammonium salt, both the RT-PCR and PCR produced an amplified fragment. This indicates that the strong chaotropic substances and ammonium salt inhibited the DNase I treatment. Accordingly, the strong chaotropic substances and ammonium salt are not preferred as additives for the reagents for RNA extraction in the present system. It is demonstrated that in the case of containing no RNA protecting agent salt, RNA was degraded and neither the RT-PCR nor PCR produced an amplified fragment.

Comparative Example 2

Following the procedure described below, RNA was extracted from mouse blood, and RT-PCR was performed using the extracted RNA as a template. Agarose gel electrophoresis was then performed to confirm the presence of an amplified fragment.
(Preparation of Reagent for RNA Extraction)
A reagent for RNA extraction having the following composition and free from surfactants was prepared: 0.7 M lithium chloride, 75 mM TAPS (pH 8.0), 2.25 mM $CaCl_2$, 15 mM $MgCl_2$, and 50 mM EDTA.
(Extraction of RNA)
Using the prepared reagent for RNA extraction and following the same procedure as in Example 1, blood was collected from a mouse and RNA was then extracted from the sample.
(RT-PCR)
Following the same procedure as in Example 1, RT-PCR was performed using the RNA sample extracted above as a template.

Table 2 shows the results of visualization of the amplified fragment by agarose gel electrophoresis. The results demonstrate that in the case of the reagent for RNA extraction free from surfactants, both the RT-PCR and PCR produced an amplified fragment. This is because the analyte was not completely dissolved because of the absence of surfactants, and the DNA could not be completely removed by DNase I.

Example 3 Extraction of RNA from Cultured Cells

Following the procedure described below, RNA was extracted from cultured human HEK293T cells and Jurkat cells, and agarose gel electrophoresis was then performed to confirm its presence.
(Preparation of Reagent for RNA Extraction)
A reagent for RNA extraction having the following composition with lithium chloride was prepared: 0.7 M lithium chloride, 75 mM TAPS (pH 8.0), 2.25 mM $CaCl_2$, 15 mM $MgCl_2$, 175 mM glycolic acid, 5 mM deoxycholic acid, 50 mM EDTA, and 0.05% Triton X-100.
(Extraction of RNA)
The cultured cells in an amount of $10^3$ to $10^5$ cells were centrifuged and collected as pellets. To the cell pellets was added 18 µl of the reagent for RNA extraction, and the resulting solution was incubated at 75° C. for 5 minutes. After incubation, the solution was cooled to room temperature and mixed with 2 µl (corresponding to 10 Units) of DNase I, and the mixture was incubated at 42° C. for 5 minutes and then at 75° C. for 10 minutes.
(RT-PCR)
The RNA samples prepared as above were cooled to room temperature, and RT-PCR was performed using the samples as templates to obtain amplified nucleic acid fragments derived from the respective cells. The target of RT-PCR was ACTB mRNA, and the primer set used was Forward Primer F2 (5'-AGATGGCCACGGCTGCT-3'; SEQ ID NO:3) and Reverse Primer R2 (5'-AACCGCTCATTGCCAATGG-3'; SEQ ID NO:4). The RT-PCR was carried out using PrimeScript One Step RT-PCR Kit Ver. 2 (Takara Bio, Inc.), and the RNA samples prepared above were individually added in an amount of 2% by volume to a reaction solution and subjected to the RT-PCR. The reaction consisted of reverse transcription at 50° C. for 30 minutes, and inactivation of the reverse transcriptase at 94° C. for 1 minute, followed by 30 PCR cycles of: 94° C. for 15 seconds; 60° C. for 15 seconds; and then 72° C. for 15 seconds. As a negative control, 30 PCR cycles of: 94° C. for 15 seconds; 60° C. for 15 seconds; and then 72° C. for 15 seconds were performed without performing reverse transcription. Next, the RT-PCR products were subjected to common agarose gel electrophoresis to visualize the amplified fragments.

FIG. 1 shows the amplified fragments visualized by agarose gel electrophoresis. The results demonstrate that in both the case of the HEK293T cell sample and the Jurkat cell sample, a specific amplified fragment was produced. This indicates that the respective RNAs were properly extracted.

The invention claimed is:

1. A reagent for RNA extraction from a biological sample, comprising:

an alkali metal salt in a concentration of 0.5 to 5.0 M, wherein the alkali metal salt is lithium chloride; and a surfactant, wherein the surfactant comprises an anionic surfactant of glycolic acid and of deoxycholic acid.

2. A kit for RNA extraction, comprising the reagent according to claim 1.

3. A method for RNA extraction from a biological sample, comprising:

mixing the biological sample with a reagent according to claim 1 for RNA extraction; and extracting the RNA from the biological sample.

* * * * *

UNITED STATES PATENT AND TRADEMARK OFFICE
CERTIFICATE OF CORRECTION

PATENT NO. : 9,695,413 B2
APPLICATION NO. : 14/437936
DATED : July 4, 2017
INVENTOR(S) : Sotaro Sano et al.

It is certified that error appears in the above-identified patent and that said Letters Patent is hereby corrected as shown below:

On the Title Page

At (71) Applicants, amend as follows: KANEKA CORPORATION, Osaka (JP).

Signed and Sealed this
Third Day of October, 2017

Joseph Matal
*Performing the Functions and Duties of the*
*Under Secretary of Commerce for Intellectual Property and*
*Director of the United States Patent and Trademark Office*